(12) United States Patent
Arbiser

(10) Patent No.: US 6,673,843 B2
(45) Date of Patent: *Jan. 6, 2004

(54) CURCUMIN AND CURCUMINOID INHIBITION OF ANGIOGENESIS

(75) Inventor: Jack L. Arbiser, Atlanta, GA (US)

(73) Assignee: Emory University, Atlanta, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/345,712

(22) Filed: Jun. 30, 1999

(65) Prior Publication Data

US 2002/0006966 A1 Jan. 17, 2002

(51) Int. Cl.[7] .......................... A61K 31/12; A61K 13/00
(52) U.S. Cl. ....................................... 514/679; 424/422
(58) Field of Search ........................... 514/679; 424/422

(56) References Cited

U.S. PATENT DOCUMENTS

| | | | |
|---|---|---|---|
| 4,704,383 A | | 11/1987 | McNamara et al. |
| 4,900,815 A | | 2/1990 | Tanaka et al. |
| 4,925,833 A | | 5/1990 | McNamara et al. |
| 4,935,411 A | | 6/1990 | McNamara et al. |
| 4,975,422 A | | 12/1990 | Kanoh et al. |
| 5,290,807 A | | 3/1994 | Folkman et al. |
| 5,401,504 A | | 3/1995 | Das et al. |
| 5,576,330 A | | 11/1996 | Buzzetti et al. |
| 5,629,340 A | | 5/1997 | Kuwano et al. |
| 5,639,725 A | | 6/1997 | O'Reilly |
| 5,654,312 A | * | 8/1997 | Andrulis, Jr. et al. ....... 514/279 |
| 5,670,493 A | | 9/1997 | Cordi et al. |
| 5,712,291 A | | 1/1998 | D'Amato |
| 5,733,876 A | | 3/1998 | O'Reilly et al. |
| 5,861,415 A | * | 1/1999 | Majeed et al. .............. 514/321 |
| 5,891,924 A | | 4/1999 | Aggarwal |
| 5,925,376 A | * | 7/1999 | Heng ......................... 424/451 |

FOREIGN PATENT DOCUMENTS

| | | | |
|---|---|---|---|
| JP | 06128133 A | * | 5/1994 |
| JP | 10120558 A | * | 10/1996 |
| JP | 10120558 A | * | 5/1998 |
| JP | 11-92363 | * | 4/1999 |
| JP | 11092363 | * | 4/1999 |
| WO | 9518606 | * | 7/1995 |

OTHER PUBLICATIONS

Dipiro et al. Pharmacotherapy A Pathophysiologic Approach. 1989 . pp. 960–961.*

Arbiser et al. "Curcumin is an in vivo inhibitor of angiogenesis"; Molecular Medicine , vol. 4, No. 6, pp. 376–383; ISSN: 1076–1551, Jun. 1998.*

Arbiser, et al., "Oncogenic H–ras stimulates tumor angiogenesis by two distinct pathways," Proc Natl Acad Sci U S A. 94(3):861–6 (1997).

Bille, et al., "Subchronic oral toxicity of turmeric oleoresin in pigs," Food Chem Toxicol. 23(11):967–73 (1985).

Conney, et al., "Inhibitory effect of curcumin and some related dietary compounds on tumor promotion and arachidonic acid metabolism in mouse skin," Adv. Enzyme Regul. 31:385–96 (1991).

Elayan, et al., "Long–term alteration in the central monoaminergic systems of the rat by 2,4,5–trihydroxyamphetamine but not by 2–hydroxy–4,5–methylenedioxymethamphetamine or 2–hydroxy–4,5–methylenedioxyamphetamine," Eur. J. Pharmacol. 221 (2–3):281–8 (1992).

Folkman, "Antiangiogenic gene therapy," Proc. Natl. Acad. Sci. U. S. A. 95(16):9064–6 (1998).

Folkman, "Diagnostic and therapeutic applications of angiogenesis research," C. R. Acad. Sci. III. 316(9):914–18 (1993).

Folkman, et al., "Long–term culture of capillary endothelial cells," Proc. Natl. Acad. Sci. U. S. A. 76(10):5217–21 (1979).

Genetic Engineering News, 18(17):1, 8, 34, 46 (1998).

Golub, et al., "A non–antibacterial chemically–modified tetracycline inhibits mammalian collagenase activity," J. Dent. Res. 1987 Aug;66(8):1310–4.

Golub, et al., "Further evidence that tetracyclines inhibit collagenase activity in human crevicular fluid and from other mammalian sources," J. Periodontal Res. 20(1):12–23 (1985).

Golub, et al., "Minocycline reduces gingival collagenolytic activity during diabetes. Preliminary observations and a proposed new mechanism of action," J. Periodontal Res. 18(5):516–26 (1983).

(List continued on next page.)

Primary Examiner—Theodore J. Criares
Assistant Examiner—Jennifer Kim
(74) Attorney, Agent, or Firm—Holland & Knight LLP

(57) ABSTRACT

Methods for treating diseases or disorders of the skin which are characterized by angiogenesis have been developed using curcumin and curcumin analogs. Based on the results obtained with curcumin, it has been determined that other angiogenesis inhibitors can also be used to treat these skin disorders. It has further been discovered that curcumin acts to inhibit angiogenesis in part by inhibition of basic fibroblast growth factor (bFGF), and thereby provides a means for treating other disorders characterized by elevated levels of bFGF, such as bladder cancer, using curcumin and other analogues which also inhibit bFGF. Representative skin disorders to be treated include the malignant diseases angiosarcoma, hemangioendothelioma, basal cell carcinoma, squamous cell carcinoma, malignant melanoma and Karposi's sarcoma, and the non-malignant diseases or conditions including psoriasis, lymphangiogenesis, hemangioma of childhood, Sturge-Weber syndrome, verruca vulgaris, neurofibromatosis, tuberous sclerosis, pyogenic granulomas, recessive dystrophic epidermolysis bullosa, venous ulcers, acne, rosacea, eczema, molluscum contagious, seborrheic keratosis, and actinic keratosis.

7 Claims, 3 Drawing Sheets

OTHER PUBLICATIONS

Golub, et al., "Tetracyclines inhibit tissue collagenase activity. A new mechanism in the treatment of periodontal disease," *Periodontal Res*. 19(6):651–5 (1984).

Hong & Lippman, "Cancer chemoprevention,"*J. Natl. Cancer Inst. Monogr*. (17):49–53 (1995).

Huang, et al., "Effect of dietary curcumin and ascorbyl palmitate on azoxymethanol–induced colonic epithelial cell proliferation and focal areas of dysplasia," *Cancer Lett*. 64(2):117–21 (1992).

Huang, et al., "Effects of curcumin, demethoxycurcumin, bisdemethoxycurcumin and tetrahydrocurcumin on 12–O–tetradecanoylphorbol–13–acetate–induced tumor promotion," *Carcinogenesis* 16(10):2493–7 (1995).

Huang, et al., "Suppression of c–Jun/AP–1 activation by an inhibitor of tumor promotion in mouse fibroblast cells," *Proc. Natl. Acad. Sci. U. S. A*. 88(12):5292–6 (1991).

Kelloff, et al., "Cancer Chemopreventive Agents: Drug Development Status II," *J. Cell Biochem. Suppl*. 26:1–28 (1996).

Kent, et al., "Requirement for protein kinase C activation in basic fibroblast growth factor–induced human endothelial cell proliferation," *Circ. Res*. 77(2):231–8 (1995).

Kenyon, et al., "A model of angiogenesis in the mouse cornea," *Invest. Ophthalmol. Vis. Sci*. 37(8):1625–32 (1996).

Kilpatrick, et al., "Towards an RNA–based therapy for Marfan syndrome," *Mol. Med. Today* 4(9):376–81 (1998).

Kohl, et al., "Inhibiton of farnesyltransferase induces regression of mammary and salivary carcinomas in ras transgenic mice," *Nat. Med*. 1(8):792–7 (1995).

Korutla, et al., "Inhibition of ligand–induced activation of epidermal growth factor receptor tyrosine phosphorylation by curcumin," *Carcinogenesis* 16(8):1741–5 (1995).

Larcher, et al., "Up–regulation of vascular endothelial growth factor/vascular permeability factor in mouse skin carcinogenesis correlates with malignant progression state and activated H–ras expression levels," *Cancer Res*. 56(23):5391–6 (1996).

Lu, et al., "Effect of curcumin on 12–O–tetradecanoylphorbol–13–acetate–and ultraviolet b light–induced expression of c–Jun and c–Fos in JB6 cells and in mouse epidermis," *Carcinogenesis* 15(10):2363–70 (1994).

Martell & Boothe, "The 6–deoxytetracyclines. VII. Alkylated aminotetracyclines possessing unique antibacterial activity," *J. Med. Chem*. 10(1):44–6 (1967).

O'Brien, et al. "Two mechanisms of basic fibroblast growth factor–induced angiogenesis in bladder cancer," *Cancer Res*. 57(1):136–40 (1997).

Prochaska, et al., "Rapid detection of inducers of enzymes that protect against carcinogens," *Proc. Natl. Acad. Sci. U. S. A*. 89(6):2394–8 (1992).

Rao, et al., "Chemoprevention of colon carcinogenesis by dietary curcumin, a naturally occurring plant phenolic compound," *Cancer Res*. 55(2):259–66 (1995)

Rao, et al., "Inhibition by dietary curcumin of azoxymethane–induced ornithine decarboxylase, tyrosine protein kinase, arachidonic acid metabolism and aberrant crypt foci formation in the rat colon," *Carcinogenesis* 14(11):2219–25 (1993).

Rao, et al., "Anti–inflammatory activity of curcumin analogues," *Indian J. Med. Res*. 75:574–8 (1982).

\* cited by examiner

CURCUMIN AND CURCUMINOID INHIBITION OF ANGIOGENESIS

The United States government has rights in this invention by virtue of grant R03 AR44947 from the National Institutes of Health.

BACKGROUND OF THE INVENTION

The invention is generally in the field of methods of inhibiting angiogenesis, and more specifically is drawn to methods and compositions for inhibiting angiogenesis.

Current treatments of cancer and related diseases have limited effectiveness and numerous serious unintended effects. Based primarily on chemical, radiation and surgical therapy, these treatments have progressed only incrementally during more than thirty years of intensive research to discover the origins and devise improved therapies of neoplastic diseases.

Current research strategies emphasize the search for effective therapeutic modes with less risk, including the use of natural products and biological agents. This change in emphasis has been stimulated by the fact that many of the consequences, to patients and their offspring, of conventional cancer treatment, including new cancers, mutations and congenital defects, result from their actions on genetic material and mechanisms. Hong et al., J. Natl. Cancer Inst. Monogr. 17:49–53 (1995). Efforts continue to discover the origins of cancer at the genetic level, and correspondingly new treatments, but such interventions also may have serious unanticipated effects.

The observation by Folkman that tumors are highly vascular, and the elucidation by him and others of a process termed angiogenesis through which many tumors derive a blood supply by the generation of microvessels, provided an important new avenue to therapy of cancer and other diseases and disorders. Folkman, Proc. Natl. Acad. Sci. U.S.A. 95(16):9064–6 (1998); C. R. Acad. Sci. III 316(9):909–918 (1993). Angiogenesis has now been recognized in inflammatory lesions and benign tumors, in addition to malignant tumors.

Mammals are characterized by complex cardiovascular systems that enable their warm-blooded nature, internal embryonic and fetal development and successful population of extreme habitats. The development of an extensive capillary system, specialized in each organ and tissue, is an essential feature of mammalian cardiovascular systems, to provide optimal distribution of nutrients and other substances including hormones and defensive agents. The metabolic and physiologic needs of mammalian cells are met by their proximity to capillaries, and limited resources may be diverted by imbalance of this supply system. Tortora, "Principles of Human Anatomy", 5$^{th}$ ed., pp. 371–372, Harper & Row, N.Y. (1989).

Angiogenesis results primarily from the development of new or lengthened capillaries, and larger microvessels. Capillaries are formed primarily of specialized endothelial cells and the connective tissue layer to which they adhere, the basement membrane. The proliferation of endothelial cells and their migration and orientation to form capillaries is recognized as the key process regulated in the control of angiogenesis. Neovascularization is a form of angiogenesis marked by formation of blood vessels in a tissue or region previously devoid of blood vessel supply, for example the cornea of the eye. The mechanisms involved in angiogenesis are quite complicated, however, and no one appears to be the sole controlling mechanism.

Mammals have effective mechanisms to regulate this vital process. Stimulation of angiogenesis in adult mammals, other than as a part of normal tissue repair, pregnancy or the menstrual cycle, is abnormal and often pathological. Many malignant tumors, benign tumors and inflammatory lesions have the ability to evade or mobilize these regulatory mechanisms to support their growth and further malignant progression.

Development of effective preventive and treatment means has been hampered by inadequate understanding of the factors controlling this process. The premise of therapeutic development for such conditions is that effective treatment does not require destruction of the cells or tissues of origin. Reduction or prevention of the increased blood supply can be sufficient to prevent their growth, and the manifestation of the condition as a disease or pathological disorder.

This concept was initially rejected, but widespread recognition of angiogenesis as a major factor in a variety of pathological conditions and diseases, particularly cancer and pre-cancerous conditions, has occurred recently among scientists and businesses. It is estimated that 184 million U.S. and European Union (EU) disease cases could benefit from treatment to inhibit angiogenesis that is inappropriate and pathological (anti-angiogenic therapy), in addition to an estimated 314 million disease cases in the U.S. and EU that might benefit from treatment to stimulate angiogenesis, for example in cardiac rehabilitation. Thirty-one specific projects of pharmaceutical and biotechnology companies to develop anti-angiogenic treatment were reported in Gen. Eng. News 18(17):1, 8, 34, 46 (1998).

It is an object of the present invention to provide methods of treating a mammal having a disease or condition characterized by increased angiogenesis.

It is a further object of the present invention to provide a method of preventing the initiation or progression of a disease or condition characterized by increased angiogenesis in a mammal, especially skin diseases and diseases characterized by elevated basic fibroblast growth factor.

SUMMARY OF THE INVENTION

Methods for treating diseases or disorders of the skin which are characterized by angiogenesis have been developed using curcumin and curcumin analogs. Based on the results obtained with curcumin, it has been determined that other angiogenesis inhibitors can also be used to treat these skin disorders. It was also discovered that curcumin acts to inhibit angiogenesis in part by inhibition of basic fibroblast growth factor (bFGF), and thereby provides a means for treating other disorders characterized by elevated levels of bFGF, such as bladder cancer, using curcumin and other analogues which also inhibit bFGF.

Curcumin and demethoxycurcumin are the preferred agents for treating these disorders. The preferred means of administration is to apply the curcumin topically, for example, as an ointment or hydrogel containing between one-half percent (0.5%) and five percent (5%) of the curcumin, or regionally, orally to treat disorders of the gastrointestinal tract or by instillation, to treat bladder or cervical cancer. In alternative embodiments, the curcumin or its analogs can be implanted in the form of one or more pellets of a pharmaceutically acceptable vehicle encapsulating or encorporating the curcumin, or by one or more injections of a pharmaceutically acceptable aqueous solution including the curcumin.

Representative skin disorders include the malignant diseases angiosarcoma, hemangioendothelioma, basal cell carcinoma, squamous cell carcinoma, malignant melanoma and Karposi's sarcoma, and the non-malignant diseases or conditions including psoriasis, lymphangiogenesis, hemangioma of childhood, Sturge-Weber syndrome, verruca vulgaris, neurofibromatosis, tuberous sclerosis, pyogenic granulomas, recessive dystrophic epidermolysis bullosa, venous ulcers, acne, rosacea, eczema, molluscum contagious, seborrheic keratosis, and actinic keratosis. Representative disorders characterized by increased levels of bFGF include bladdar and cervical cancers.

As demonstrated in the examples, curcumin and its analogs are potent inhibitors of endothelial cell proliferation, a sensitive test of in vitro antiangiogenic effectiveness, and also of corneal neovascularization, a sensitive and reliable test of in vivo antiangiogenic effectiveness. The examples demonstrate that this inhibition is exerted directly on the endothelial cells that are primarily involved in angiogenesis, and not indirectly through other effects of these agents. The examples further demonstrate that curcumin and its analogs inhibit the stimulation of angiogenesis in vivo by basic fibroblast growth factor.

BRIEF DESCRIPTION OF THE DRAWINGS

FIG. 1A), in the presence of bFGF (FIG. 1B) and in the absence of bFGF, where the endothelial cells have been transformed (FIG. 1C). The figures are graphs of cell number versus concentration of curcumin ($\mu$M).

DETAILED DESCRIPTION OF THE INVENTION

I. Disorders to be Treated

Figure 1A:
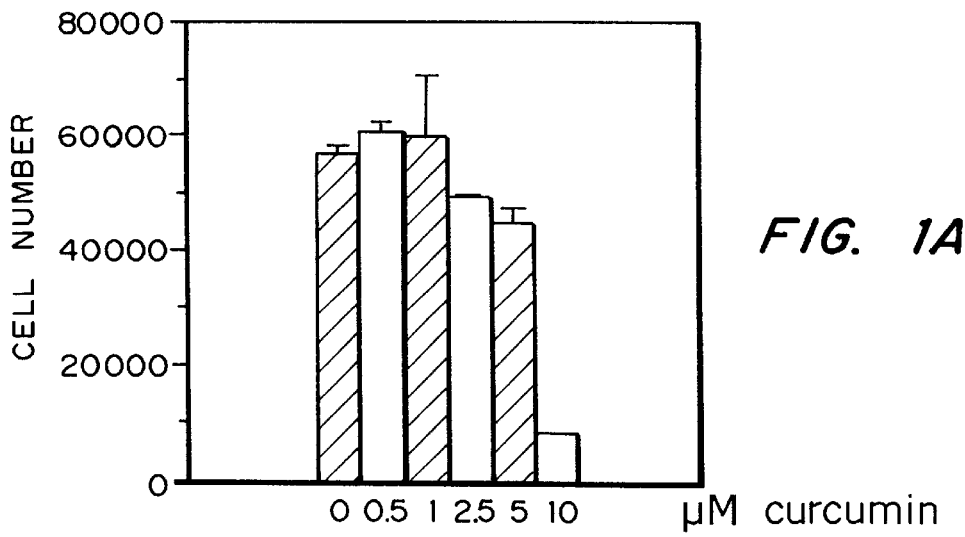
FIGS. 1A–C describe the effect of curcumin on endothelial cell proliferation in the absence of basic fibroblast growth factor (bFGF.

Disorders or diseases that can be treated with the angiogenesis inhibitors include those characterized by elevated levels of basic fibroblast growth factor (bFGF), and a number of dermatological disorders.

Diseases and pathological disorders of the skin characterized by angiogenesis in humans include the malignant diseases angiosarcoma, hemangioendothelioma, basal cell carcinoma, squamous cell carcinoma, malignant melanoma and Karposi's sarcoma, and the non-malignant diseases or conditions psoriasis, lymphangiogenesis, hemangioma of childhood, Sturge-Weber syndrome, verruca vulgaris, neurofibromatosis, tuberous sclerosis, pyogenic granulomas, recessive dystrophic epidermolysis bullosa, venous ulcers, acne, rosacea, eczema, molluscum contagious, seborrheic keratosis, and actinic keratosis.

Examples of disorders characterized by elevated levels of bFGF include bladder cancer (O'Brien, et al. Cancer Res. 57(1):136–140 (1997)) and cervical cancer (which is caused by a herpes papilloma virus, known to elicit elevated levels of bFGF).

II. Pharmaceutical Compositions

A. Angiogenesis Inhibitors

Several different classes of compounds have been determined to be useful as inhibitors of angiogenesis. These include collagenase inhibitors such as metalloproteinases and tetracyclines such as minocycline, naturally occurring peptides such as endostatin and angiostatin, described for example in U.S. Pat. No. 5,733,876 to O'Reilly, et al., U.S. Pat. No. 5,290,807, and U.S. Pat. No. 5,639,725, fungal and bacterial derivatives, such as fumagillin derivatives like TNP-470, the sulfated polysaccharides described in U.S. Pat. No. 4,900,815 to Tanaka, et al. and the protein-polysaccharides of U.S. Pat. No. 4,975,422 to Kanoh, et al. and synthetic compounds such as the 2,5-diaryltetrahydrofurans of U.S. Pat. No. 5,629,340 to Kuwano, et al., aminophenylphosphonic acid compounds of U.S. Pat. No. 5,670,493 to Cordi, et al., the 3-substituted oxindole derivatives of U.S. Pat. No. 5,576,330 to Buzzetti, et al., and thalidomides of U.S. Pat. No. 5,712,291 to D'Amato.

The antibiotics that are useful as angiogenesis inhibitors are those having collagenase inhibitory activity. These include the tetracyclines and chemically modified tetracyclines (CMTs), and three ringed tetracycline homologs, that have the ability to inhibit collagenase but diminished antibacterial activity. Examples of commercially available tetracyclines include chlotetracyline, demeclyeycline, doxycycline, lymecycline, methacycline, minocycline, oxytetracycline, rolitetracycline, and tetracycline. The active salts, which are formed through protonation of the dimethylamino group on carbon atom 4, exist as crystalline compounds. These are stabilized in aqueous solution by addition of acid.

Minocycline, a semisynthetic tetracycline antimicrobial, described by Martell, M. J., and Boothe, J. H. in *J. Med. Chem.*, 10:44–46 (1967), and Zbinovsky, Y., and Chrikian, G. P. Minocycline. In: K. Florey (ed.), *Analytical Profiles of Drug Substances*, pp. 323–339 (Academic Press, NY 1977), the teachings of which are incorporated herein, has anticollagenase properties, as reported by Golub. L. M., et al., *J. Periodontal Res.*, 18:516–526 (1983); Golub, L. M., et al., *J. Periodontal Res.* 19:651–655 (1984); Golub, L. M., et al., *J. Periodontal Res.* 20:12–23 (1985); and Golub, L. M., et al., *J. Dent. Res.*, 66:1310–1314 (1987). Minocycline, first described in 1967, is derived from the naturally produced parent compounds chlortetracycline and oxytetracycline. The chemically modified tetracyclines are described by U.S. Pat. No. 4,704,383 to McNamara, et al., U.S. Pat. No. 4,925,833 to McNamara, et al., and U.S. Pat. No. 4,935,411 to McNamara, et al., the teachings of which are incorporated herein.

Other exemplary anti-angiogenic compounds include penicillamine and some cytokines such as IL 12.

Angiogenesis inhibitors may be divided into at least two classes. The first class, direct angiogenesis inhibitors, includes those agents which are relatively specific for endothelial cells and have little effect on tumor cells. Examples of these include soluble vascular endothelial growth factor (VEGF) receptor antagonists and angiostatin. Basic fibroblast growth factor (bFGF) is a potent, direct angiogenic factor, which has been shown to be a strong stimulus for both endothelial proliferation and migration, in vitro and in vivo. The activity of bFGF on endothelial cells may be due in part to stimulation of protein kinase C. Shing et al., Science 223:1296–1299 (1984); Kent et al., Circ. Res. 77:231–238 (1995). Blockage of bFGF's stimulation of endothelial cells can inhibit angiogenesis.

Indirect inhibitors may not have direct effects on endothelial cells but may down-regulate the production of an angiogenesis stimulator, such as VEGF. Arbiser et al., Molec. Med. 4:376–383 (1998). VEGF has been shown to be up-regulated during chemically induced skin carcinogenesis; this is likely due to activation of oncogenes, such as H-ras. Arbiser et al., Proc. Natl. Acad. Sci. U.S.A. 94:861–866 (1997); Larcher et al., Cancer Res. 56:5391–5396 (1996); Kohl et al., Nature Med. 1:792–797 (1995). Examples of indirect inhibitors of angiogenesis include inhibitors of ras-mediated signal transduction, such as farnesyltransferase inhibitors.

Direct inhibition of endothelial cell proliferation can be assayed in cell culture systems, in which the effects of specific factors which control the complex process of angiogenesis can be studied. Effects discovered in such in vitro systems can then be studied in in vivo systems. Kenyon et al., Invest. Ophthalmol. 37:1625–1632 (1996).

Curcumin (diferuloylmethane) and certain of its analogs, together termed curcuminoids, are well known natural products, recognized as safe for ingestion by and administration to mammals including humans. Bille et al., Food Chem. Toxicol. 23:967–971 (1985). Curcumin is a yellow pigment found in the rhizome of *Curcuma longa*, the source of the spice turmeric. Turmeric has been a major component of the diet of the Indian subcontinent for several hundred years, and the average daily consumption of curcumin has been found to range up to 0.6 grams for some individuals, without reported adverse effects. Food-grade curcumin consists of the three curcuminoids in the relative amounts: 77% curcumin, 17% demethoxycurcumin, and 3% bisdemethoxycurcumin.

Thimmayamma et al., Indian J. Nutr Diet 20:153–162 (1983); Bille et al., Food Chem. Toxicol. 23:967–971 (1985). The fully saturated derivative tetrahydrocurcumin is also included in the term curcuminoid.

Curcumin can be obtained from many sources, including for example Sigma-Aldrich, Inc. The curcumin analogs demethoxycurcumin, bisdemethoxycurcumin and tetrahydrocurcumin can also be obtained from many sources, or readily prepared from curcumin by those skilled in the art.

Curcumin has been used in indigenous Indian medicine for several hundred years, as a topical agent for sprains and inflammatory conditions, in addition to oral use to promote health and treat digestive and other disorders. Absorption of ingested or orally administered curcumin is known to be limited, and absorbed curcumin is rapidly metabolized. Govindarajan, CRC Critical Rev. Food Sci Nutr. 12:199–301 (1980); Rao et al., Indian J. Med. Res. 75:574–578 (1982).

Numerous effects of the ingestion or oral administration of the curcuminoids have been reported, based on controlled research, population studies, case reports and anecdotal information. Evidence of chemopreventive activity of curcumin administered orally has led to clinical trials sponsored by the National Cancer Institute, regarding prevention of cancer. Kelloff et al., J. Cell. Biochem. Suppl. 26:1–28 (1996). Oral administration of curcumin to mice treated with skin and colon chemical carcinogens has been shown to result in a decreased incidence and size of induced tumors compared with control mice. Huang, et al., Cancer Res. 54:5841–5847 (1994); Huang et al., Carcinogenesis 16:2493–2497 (1995); Huang et al., Cancer Lett. 64:117–121; Rao et al., Cancer Res. 55:259–266 (1995); Conney et al., Adv Enzyme Regul. 31:385–396 (1991).

Huang, et al. found that the oral administration of three curcuminoid compounds curcumin, demethoxycurcumin and bisdemethoxycurcumin were able to inhibit phorbol ester-stimulated induction of ornithine decarboxylase and promotion of mouse skin initiated with 7,12-dimethylbenzanthracene (DMBA). These compounds also inhibited phorbol ester-mediated transformation of JB6 cells. The saturated derivative tetrahydrocurcumin was less active than the unsaturated analogs in these assays. Huang et al., Carcinogenesis 16:2493–2497 (1995).

The mechanism or mechanisms of curcumin's chemopreventive activities were not previously understood, although it was recognized as an antioxidant and was known to exhibit antimutagenic activity in the Ames Salmonella test and to produce biochemical effects similar to those of the polyphenols, chemopreventive agents found in green tea. Stoner, J. Cell. Biochem. Suppl. 22:169–180 (1995). Curcumin has been demonstrated to inhibit several signal transduction pathways, including those involving protein kinase, the transcription factor NF-kB, phospholipase A2 bioactivity, arachidonic acid metabolism, antioxidant activity, and epidermal growth factor (EGF) receptor autophosphorylation. Lu et al., Carcinogenesis 15:2363–2370 (1994); Singh et al., J. Biol. Chem. 270:24995–25000 (1995); Huang et al., Proc. Natl. Acad. Sci. U.S.A. 88:5292–5296 (1991); Korutla et al., Carcinogenesis 16:1741–1745 (1995); Rao et al., Carcinogenesis 14:2219–2225 (1993).

Because of the complexity of the factors that regulate or effect angiogenesis, and their specific variation between tissues and according to circumstances, the response to a specific agent may be different or opposite, in different tissues, under different physiological or pathological conditions and between in vitro and in vivo conditions. For example, U.S. Pat. No. 5,401,504 to Das et al., discloses that oral or topical administration of turmeric to animals including humans promotes wound healing, and postulates that it acts in part through stimulation of angiogenesis, although this postulate was not experimentally verified. Administration of curcumin has been reported to inhibit smooth muscle cell proliferation in vitro. Huang, et al., European J. Pharmac. 221:381–384 (1992). U.S. Pat. No. 5,891,924 to Aggarwal discloses that oral administration of curcumin to animals inhibits activation of the transcription factor NF-kB, and claims its use in pathophysiological states, particularly specific conditions involving the immune system. Several biochemical actions of curcumin were studied in detail, but no single action was reported to be responsible for these effects of curcumin. Singh et al. reported that curcumin inhibits in vitro proliferation of human umbilical vein endothelial cells (HUVEC) and suggested that it might have anti-angiogenic activity. However, this inhibition was independent of basic fibroblast growth factor stimulation of the proliferation of endothelial cells, and in vivo studies were not reported. Singh et al., Cancer Lett. 107:109–115 (1996). Thaloor et al. disclosed inhibition by curcumin of HUVEC growth and formation of tube structures on Matrigel, in a model of capillary formation, and ascribed this inhibition to modulation of metalloproteinases of the HUVEC. Thaloor et al., Cell Growth Differ. 9:305–312 (1998).

As demonstrated by the examples, these are not the mechanism involved in inhibition of angiogenesis as described herein, and accordingly, the disorder to be treated and the dosage and means of administration are different, based on the role of curcuminoids in inhibiting bFGF.

B. Carriers

Pharmaceutical compositions containing the angiogenesis inhibitor are prepared based on the specific application. Application can be either topical, localized, or systemic.

Any of these compositions may also include preservatives, antioxidants, antibiotics, immunosuppressants, and other biologically or pharmaceutically effective agents which do not exert a detrimental effect on the normal tissue to be treated.

Compositions for local or systemic administration will generally include an inert diluent. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

Systemic Carriers

Inhibitors can be systemically administered either parenterally or enterally. The composition can be administered by means of an infusion pump, for example, of the type used for delivering insulin or chemotherapy to specific organs or tumors, by injection, or by depo using a controlled or sustained release formulation. In a preferred systemic embodiment, drugs are administered orally, in an enteric carrier if necessary to protect the drug during passage through the stomach.

The angiogenic inhibitors can be administered systemically by injection in a carrier such as saline or phosphate buffered saline (PBS) or orally, in the case of an inhibitor such as thalidomide, in tablet or capsule form. The tablets or capsules can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; or a glidant such as colloidal silicon dioxide. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

Local or Topical Carriers

The angiogenic inhibitors can also be applied locally or topically, in a carrier such as saline or PBS, in an ointment or gel, in a transdermal patch or bandage, or controlled or sustained release formulation. Local administration can be by injection at the site of the injury, or by spraying topically onto the injury. The inhibitor can be absorbed into a bandage for direct application to the wound, or released from sutures or staples at the site. Incorporation of compounds into controlled or sustained release formulations is well known.

For topical application, the angiogenesis inhibitor is combined with a carrier so that an effective dosage is delivered, based on the desired activity, at the site of application. The topical composition can be applied to the skin for treatment of diseases such as psoriasis. The carrier may be in the form of an ointment, cream, gel, paste, foam, aerosol, suppository, pad or gelled stick. A topical composition for use of an ointment or gel consists of an effective amount of angiogenesis inhibitor in an ophthalmically acceptable excipient such as buffered saline, mineral oil, vegetable oils such as corn or arachis oil, petroleum jelly, Miglyol 182, alcohol solutions, or liposomes or liposome-like products.

In a preferred form for controlled release, the composition is administered in combination with a biocompatible polymeric implant which releases the angiogenesis inhibitor over a controlled period of time at a selected site. Examples of preferred biodegradable polymeric materials include polyanhydrides, polyorthoesters, polyglycolic acid, polylactic acid, polyethylene vinyl acetate, and copolymers and blends thereof. Examples of preferred non-biodegradable polymeric materials include ethylene vinyl acetate copolymers. These can be prepared using standard techniques as microspheres, microcapsules, tablets, disks, sheets, and fibers.

An implantable pellet is the preferred mode of local administration of these agents to tissues. The preferred concentration of curcuminoid agent delivered locally to the target tissue is greater than 10 micromolar, preferably 10–50 micromolar.

III. Methods for Treatment

For the treatment of skin disorders, the angiogenesis inhibitors are administered topically or regionally. In a preferred embodiment, the inhibitors are administered in an ointment, salve or other pharmaceutically acceptable carrier. For treatment of certain disorders characterized by elevated levels of bFGF, the angiogenesis inhibitors, preferably curcumin or demethoxycurcumin or another curcuminoid compound, or a combination of two or more curcuminoid compounds, is applied topically in diseases or pathologic conditions of the skin, or locally in other tissues, to treat cancer, pre-malignant conditions and other diseases and conditions in which angiogenesis occurs. The preferred means of administration is to apply the curcumin topically, for example, as an ointment or hydrogel containing between one-half percent (0.5%) and five percent (5%) of the curcumin, or regionally, orally to treat disorders of the gastrointestinal tract or by instillation, to treat bladder or cervical cancer.

The administration of these agents topically or locally may also used to prevent initiation or progression of such diseases and conditions. For example, a curcuminoid formulation may be administered topically or by instillation into a bladdar if a biopsy indicated a pre-cancerous condition or into the cervix if a Pap smear was abnormal or suspicious.

The angiogenesis inhibiting formulation is administered as required to alleviate the symptoms of the disorder. Assays can be performed to determine an effective amount of the agent, either in vitro and in vivo. Representative assays are described in the examples provided below. Other methods are known to those skilled in the art, and can be used to determine an effective dose of these and other agents for the treatment and prevention of diseases or other disorders as described herein.

The present invention will be further understood by reference to the following non-limiting examples.

As demonstrated in the examples, curcumin inhibits basic fibroblast growth factor (bFGF)-induced proliferation of endothelial cells in vitro and angiogenesis in vivo. The effect of curcumin and curcumin analogs with known differential chemopreventive activities, demethoxycurcumin, tetrahydrocurcumin, and bisdemethoxycurcumin, on in vivo angiogenesis was also demonstrated. Curcumin had a strong antiproliferative effect on endothelial cells, with a steep curve occurring between 5 and 10 $\mu$M. This was true both in the presence or absence of bFGF, and this inhibition could not be overcome by the immortalizing ability of SV40 large T antigen. The corneal neovascularization assay, which measures increased vessel length and density in vivo, in response to a bFGF pellet placed in the normally avascular cornea, has proven useful in the confirmation and characterization of multiple angiogenesis inhibitors. The inhibition of bFGF-mediated corneal neovascularization by curcumin and its derivatives is evidence that curcumin is a direct angiogenesis inhibitor in vivo. This inhibition was not due to dilution of bFGF, as administration of a structurally related inactive compound, tetraphenylcyclopentadienone (TPCPD), had no effect on bFGF-induced corneal neovascularization. The lack of inhibition of TPA-mediated VEGF production further supports the role of curcumin as a direct angiogenesis inhibitor.

The following materials and methods were used in the examples.

Materials and Methods

Endothelial Proliferation Assays

Bovine capillary endothelial cells were isolated according to the method of Folkman, et al., Proc. Nat. Acad. Sci. U.S.A. 76:5217–5221 (1979), and were plated at a concentration of 10,000 cells/well in gelatinized 24-well dishes. The primary endothelial cells were cultured in Dulbecco's modified Eagle's medium (DMEM) supplemented with 10% bovine serum and grown at 37° C. in 10% CO2. Twenty-four hours after plating, cells were treated with curcumin in the presence or absence of bFGF. After 72 hours of treatment, cells were counted using a Coulter counter. Cell counts for each condition were repeated in triplicate and in the presence or absence of 1 ng/ml bFGF.

Similarly, MSI (ATCC CCRL 2279) endothelial cells, which are a SV40 large T antigen immortalized murine endothelial cell line, were also plated at a concentration of 10,000 cells/well in nongelatinized 24-well dishes. MSI cells do not require endothelial mitogens for growth and were cultured in DMEM supplemented with 5% fetal calf serum (FCS). Cells were counted after a 72-hour exposure to curcumin with the same method used for the bovine capillary endothelial cells.

Corneal Neovascularization

C57BL6 male mice (5–6 weeks old) were anesthetized with methoxyflurane prior to implantation of pellets and with 0.5% proparacaine. A central, intrastromal linear keratotomy was performed with a surgical blade, and a lamellar micropocket was prepared according to the method of Kenyon, et al. (1996). The pellet was advanced to the end of the pocket. Erythromycin ointment was placed on the operated eye to prevent infection. Eyes were examined by slit lamp on days 3–6 after implantation under general anesthesia. Corneal angiogenesis was assayed through two measurements.

Vessel length is the length of the vessel from the corneal limbus as it grows toward the pellet containing bFGF.

Sector size is a measurement of neovascularized area of the cornea. The cornea is viewed as a circle that can be divided into twelve sectors of 30 degrees span each, analogous to the division of a clock face into twelve hours. Thus, neovascularization of a sector corresponding to one fourth of the cornea would be recorded as a sector size measurement of three. This system of measurement, recording sector sizes as "clock hours", was established by Kenyon et al., Invest. Ophthalmol. 37:1625–1632 (1996).

Production of VEGF mRNA in HaCaT Keratinocytes

HaCaT keratinocytes were grown in (DMEM) (JRH) supplemented with 5% FCS (Hyclone, Logan, UT) in 25 cm² flasks. One hour prior to stimulation with 12-O-tetradecanoylphorbol-13-acetate (TPA), cells were switched to serumless media supplemented with 10 $\mu$M curcumin or an equal quantity of ethanol (final concentration 0.1%). TPA was added to a final concentration of 5 ng/ml and cells were incubated for three hours at 37° C. and harvested, and their RNA was extracted with guanidinium thiocyanate/phenol.

Phase II Enzyme Induction

The ability of curcumin derivatives to induce phase II activities was measured by assaying quinone reductase [NAD(P)H:(quinone-acceptor) oxidoreductase, EC1.6.99.2] in murine Hepa1c7 cells. Serial dilutions of curcumin, curcumin derivatives, and tetraphenylcyclopentadienone (TPCPD) were added, and the concentration of compound required to double the specific activity (CD) was calculated according to the method of Prochaska, et al., Proc. Natl. Acad. Sci. U.S.A. 89:2394–2398 (1992).

Materials

Curcumin, TPA and TPCPD were obtained from Sigma-Aldrich, Inc. Curcumin analogs (bisdemethoxycurcumin, demethoxycurcumin and tetrahydrocurcumin) were provided by Dr. A. R. Conney of Rutgers-The State University of New Jersey.

C57BL6 mice were obtained from Charles River Laboratories. The MS1 transformed cells were developed by Dr. J. L. Arbiser and deposited with the ATCC (ATCC CCRI 2279).

Implant Pellets

Pellets were prepared according to a modification of the method of Kenyon, et al. Invest. Opthalmol. Vis. Sci. 37:1625–1632 (1996). An aqueous solution of 18 mcg of basic fibroblast growth factor (Scios Nova, Mountain View, Calif.) was evaporated to dryness under reduced pressure in the presence of 10 mg of sucralfate (Bukh Meditec, Vaerlose, Denmark) Ten microliters of 12% hydron and 10 mg of curcumin or curcumin analog were then added, and the homogenous mixture was deposited onto a sterile 15×15 mm 3–300/50 Nylon mesh (Tetko, Lancaster, N.Y.) and air dried. Once the mixture was dry, the mesh was manually dissociated to yield 225 pellets. Each pellet contained 80 ng of bFGF and 44 $\mu$g of curcumin or curcumin analog. Pellets containing hydron in the absence of bFGF do not cause neovascularization, so pellets prepared in the absence of bFGF were not used in this study. The approximate pore size was 0.4×0.4 mm. Both sides of the mesh were covered with a thin layer of hydron.

Isotopically Labelled Antisense Riboprobe

A plasmid containing the coding region of human vascular endothelial growth factor (VEGF) 121 was obtained from H. Welch (University of Freiburg, Germany), and used to generate $P^{32}$-labeled antisense riboprobe as per manufacturers protocols (Ambion, Austin, Tex.). RNAse protection assays were performed according to the method of Hod, Biotechniques 13:852–853 (1992). Protected fragments were separated on gels of 5% acrylamide, 8 M urea, 1× Tris-borate buffer, and quantified with a phosphorimager (Molecular Dynamics, Sunnyvale, Calif.). An 18S riboprobe was included in each sample to normalize for variations in loading and recovery of RNA.

Measurement and Analysis

Significant differences between two groups were determined using an unpaired, two-tailed Student's t-test. Results are expressed as the mean plus or minus the standard error of the mean.

EXAMPLE 1

Curcumin Inhibition of Endothelial Cell Proliferation is Dependent on Curcumin Dose and the Presence or Absence of Basic Fibroblast Growth.

Endothelial cells were stimulated to proliferate in the presence of 1 ng/ml bFGF. Curcumin was added in concentrations ranging from 0.5 to 10 $\mu$M to primary endothelial cells.

Figure 1B:
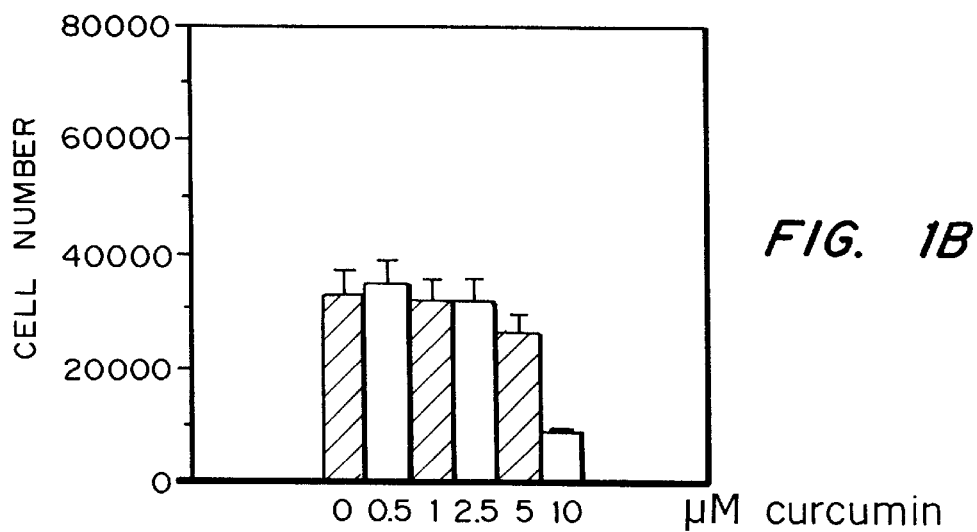
Figure 1C:
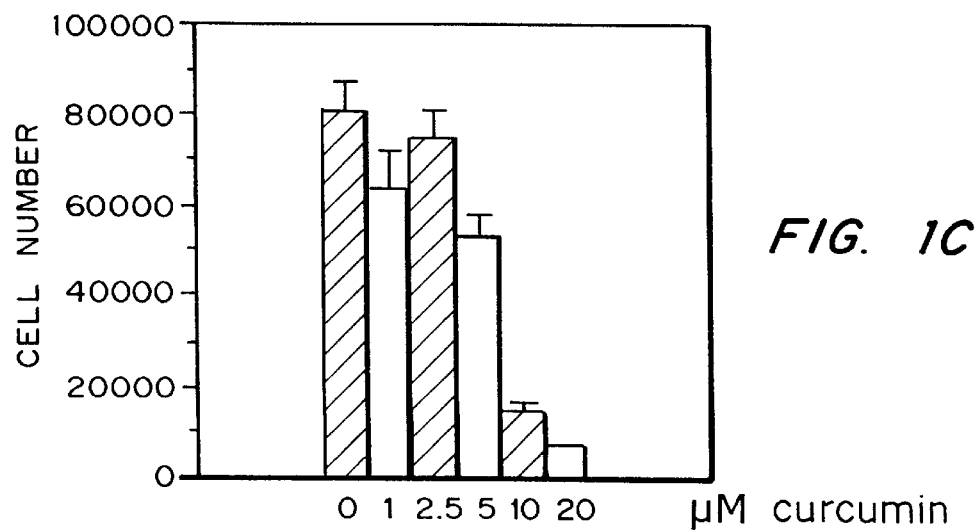

FIGS. 1A–C describe the effect of curcumin on endothelial cell proliferation in the absence of basic fibroblast growth factor (bFGF; FIG. 1A), in the absence of bFGF (FIG. 1B) and in the presence of bFGF, where the endothelial cells have been transformed (FIG. 1C). A steep decrease in cell number was seen at 10 µM. No evidence of cytotoxicity was observed, and the number of cells at the end of treatment was not significantly less than the number cells originally plated. This decrease in proliferation due to curcumin concentration of 10 µM was observed in both the presence or absence of bFGF.

In addition, curcumin was able to inhibit the growth of endothelial cells immortalized by SV40 large T antigen, with a similar dose response as seen with primary endothelial cells.

EXAMPLE 2
Curcumin Inhibition of Corneal Neovascularization is Dependent on the Presence of Basic Fibroblast Growth Factor.

The ability of curcumin to inhibit bFGF-induced corneal neovascularization in vivo was measured. Pellets were prepared containing 80 ng of bFGF and curcumin, or a control aromatic ketone, tetraphenylcyclopentadienone (TPCPD). TPCPD was added to rule out the possibility that the inhibition of neovascularization due to curcumin was not secondary to dilution. Neovascularization was assessed by slit lamp at 5 days after implantation, and the corneas were photographed.

Figure 2A:
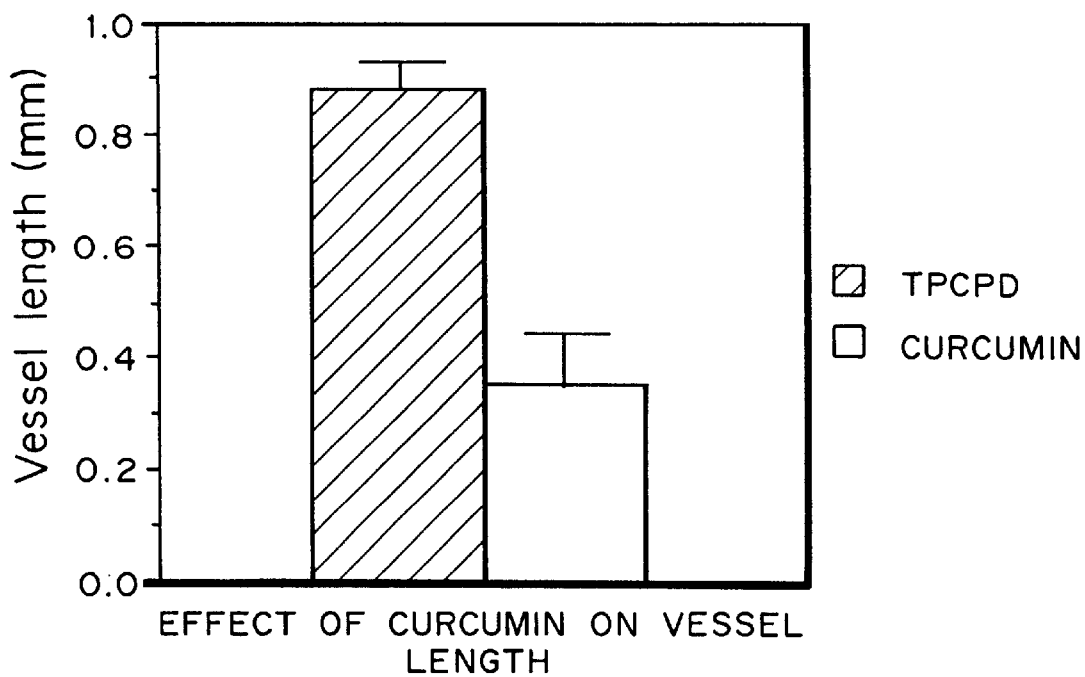
FIGS. 2A–2B describe the effect of curcumin on the extent of bFGF-stimulated neovascularization in the mouse cornea (FIG. 2A), in relation to bFGF-stimulated neovascularization in the absence of curcumin (FIG. 2B). The figures are graphs of vessel length (mm) and sector size (clock hours) comparing curcumin (10 $\mu$M) with control TPCPD, with both in the presence of 80 ng bFGF.
Figure 2B:
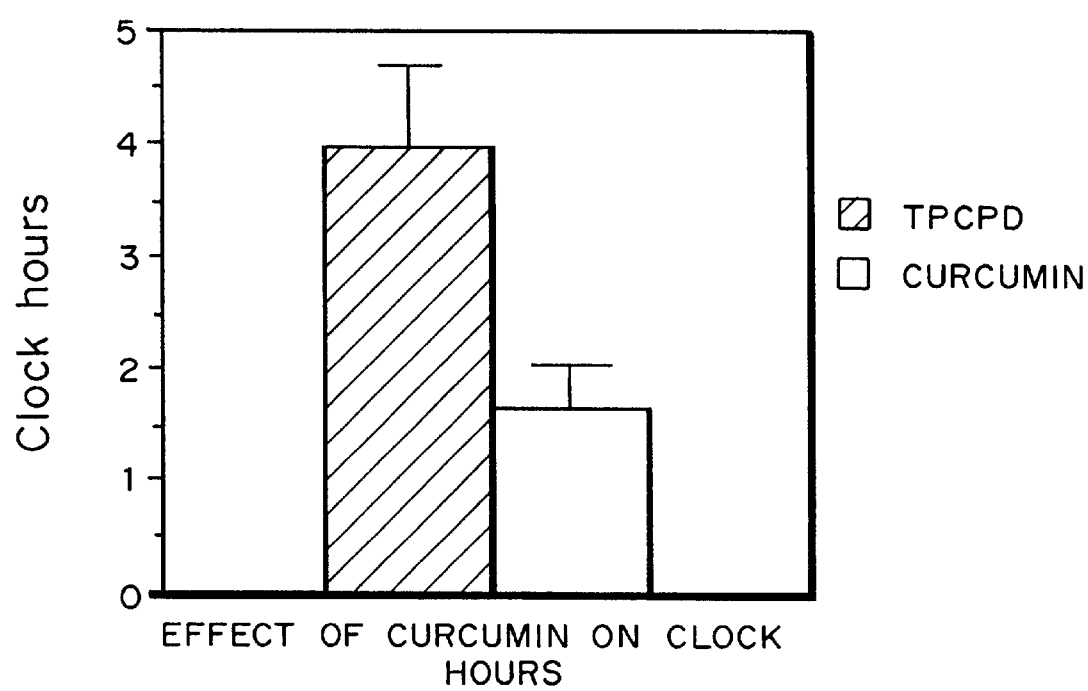

FIGS. 2A–2B describe the effect of curcumin on the extent of bFGF-stimulated neovascularization in the mouse cornea (FIG. 2A), in relation to bFGF-stimulated neovascularization in the absence of curcumin (FIG. 2B). There was no difference in neovascularization in mice containing bFGF pellets in the presence or absence of TPCPD. Both the vessel length and sectpr sizes were significantly reduced in the presence of curcumin.

EXAMPLE 3
Curcumin and Other Curcumin Analog Inhibition of Corneal Neovascularization in the Presence of Basic Fibroblast Growth Factor is Dependent on the Dose and Structure of the Curcuminoid.

Three curcumin analogs were assayed for their ability to inhibit bFGF-induced corneal neovascularization as described above.

Figure 3A:
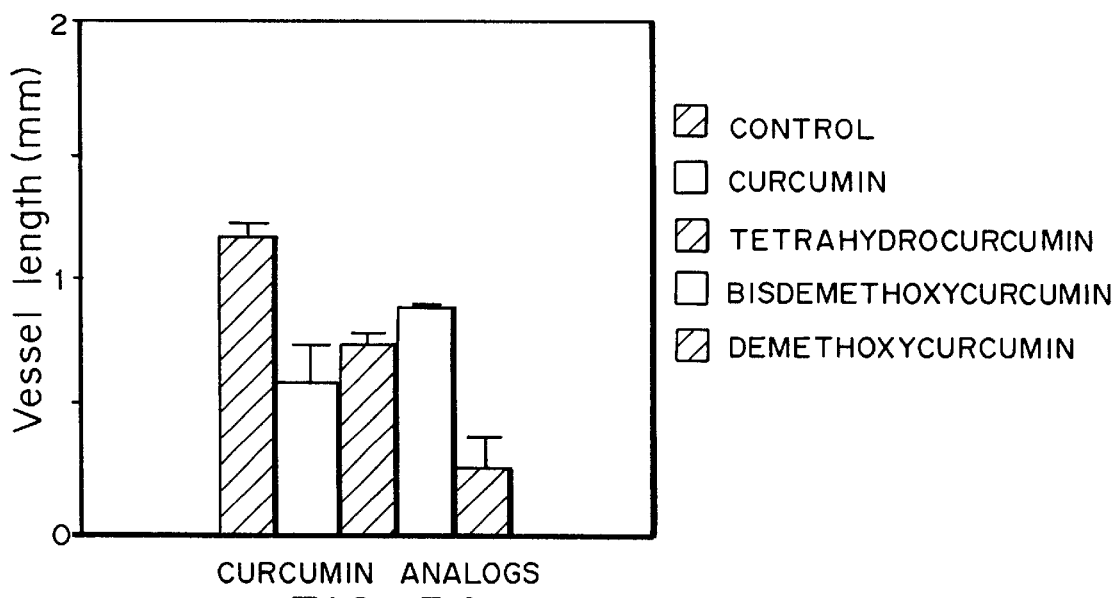
FIGS. 3A and 3B describe the effect of curcumin and other curcuminoids, tetrahydrocurcumin, bisdemethoxycurcumin, and demethoxycurcumin, on corneal neovascularization, as measured by vessel length (FIG. 3A) and by sector size (FIG. 3B).
Figure 3B:
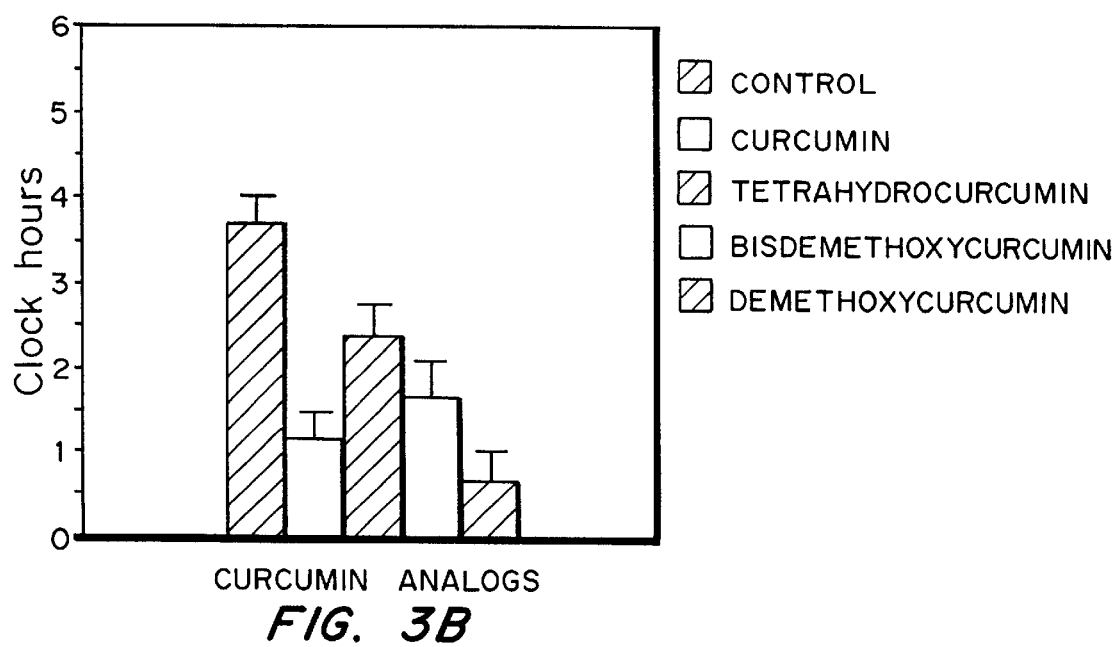

FIGS. 3A and 3B describe the effect of curcumin and other curcuminoids, tetrahydrocurcumin, bisdemethoxycurcumin, and demethoxycurcumin, on corneal neovascularization, as measured by vessel length (FIG. 3A) and by sector size (FIG. 3B). All analogs showed inhibitory activity, with demethoxycurcumin showing the greatest activity on both sector size and vessel length, tetrahydrocurcumin having the least effect on sector size, and bisdemethoxycurcumin having the least effect on vessel length. All of the curcumin analogs showed significant inhibition of bFGF-mediated neovascularization compared with control pellets.

EXAMPLE 4
Curcumin does not Inhibit Vascular Endothelial Growth Factor mRNA Production in Transformed Keratinocytes.

HaCaT cells are derived from spontaneously transformed human keratinocytes. In order to determine whether curcumin could inhibit production of angiogenesis factors by relevant tumor cells as well as directly inhibit endothelial function; HaCaT cells were treated with tetradecanoylphorbol ester (TPA) in the presence or absence of curcumin and expression of VEGF mRNA was measured.

TPA caused a 2.5-fold increase in VEGF mRNA. This increase was not inhibited by curcumin. Thus the primary antiangiogenic effect of curcumin is directly on endothelium, rather than inhibition of production of VEGF, an important angiogenic factor.

EXAMPLE 5
Inhibition of Corneal Neovascularization by Curcumin and Other Curcuminoids does not Correlate with the Induction of Phase II Enzymes by Curcumin and Other Curcuminoids.

Several plant-derived compounds with anticancer and chemopreventive activities also show the ability to induce phase II detoxifying enzymes, including quinone reductase. To determine whether the antiangiogenic activities of curcumin derivatives correlated with the ability to induce quinone reductase activity, the concentration needed to double the specific activity value (CD) was determined.

All of the curcumin analogs studied except tetrahydrocurcumin had approximately equal potencies in induction of phase II enzymes, a measure of detoxification activity, whereas the fully saturated tetrahydrocurcumin has little ability to induce phase II enzymes. Tetrahydrocurcumin, the curcumin derivative with the least antitumor activity, caused a 1.6-fold induction of quinone reductase activity at the highest concentration tested, 25 µM. However, TPCPD, which is an unsaturated aromatic ketone with no anti-angiogenic activity, had a CD value of 4.8 µM. The results are shown in Table 1. Thus, antiangiogenic activity does not correlate with phase II activity. This finding is evidence that the two processes are not based on similar mechanisms.

Modifications and variations of the methods and compositions described herein will be obvious to those skilled in the art and are intended to come within the scope of the appended claims.

TABLE 1

Actual and Relative Effects of Curcuminoids and TPCPD On Phase II Enzyme Induction and Angiogenisis

| | | | ANTI-ANGIOGENIC EFFECT | | | |
|---|---|---|---|---|---|---|
| | PHASE II INDUCTION | | Sector Size[3] | | Vessel Length | |
| COMPOUND | CD[1] | Rank[2] | (µM) | Rank[2] | (mm.) | Rank[2] |
| Tetrahydro-curcumin | >25 | 1 | 2.43 | 2 | 0.74 | 3 |
| Bisdemethoxy-curcumin | 11.0 | 2 | 1.7 | 3 | 0.88 | 2 |
| Demethoxy-curcumin | 9.0 | 3 | 0.71 | 5 | 0.26 | 5 |
| Curcumin | 7.3 | 4 | 1.17 | 4 | 0.59 | 4 |
| TPCPD | 4.8 | 5 | 3.72 | 1 | 1.16 | 1 |

Notes:
[1]Concentration to double the measured specific activity; negatively correlated with effectiveness
[2]Rank: Relative effectiveness in Phase II enzyme induction or in antiangiogenic effect (reduction of sector size or vessel length)
[3]Sector size expressed in units of 1/12 of a circle, or 30 degrees (equivalent to "clock hours")

I claim:
1. A pharmaceutical composition comprising an unsaturated curcuminoid in combination with a pharmaceutically acceptable carrier for topical administration, wherein the curcuminoid is present in a dosage effective to treat a condition selected from the group consisting of lymphangiogenesis, hemangioma of childhood, Sturge-Weber syndrome, verruca vulgaris, neurofibromatosis, tuberous sclerosis, pyogenic granulomas, recessive dystrophic epidermolysis bullosa, venous ulcers, acne, rosacea, eczema, molluscum contagious, seborrheic keratosis, and actinic keratosis, wherein the carrier is an ointment containing between one-half percent (0.5%) and five percent (5%) of the curcuminoid or a polymer formulation for implantation.

2. The composition of claim 1 the carrier is an ointment and wherein the curcuminoid is demethoxycurcumin or bisdemethoxycurcumin.

3. The composition of claim 1 as an ointment containing between one-half percent (0.5%) and five percent (5%) of the curcuminoid.

4. The composition of claim 1 wherein the carrier is a polymer formulation for implantation.

5. The composition of claim 1 wherein the curcuminoid is curcumin.

6. The composition of claim 1 wherein the curcuminoid is demethoxycurcumin.

7. The composition of claim 1 wherein the curcuminoid is bisdemethoxycurcumin.

* * * * *